United States Patent
Vanoppen et al.

(10) Patent No.: US 7,091,383 B2
(45) Date of Patent: Aug. 15, 2006

(54) METHOD FOR THE PRODUCTION OF AMINES

(75) Inventors: Dominic Vanoppen, Kapellen (BE); Ekkehard Schwab, Neustadt (DE); Frederick van Laar, Limburgerhof (DE); Hartwig Voss, Frankenthal (DE); Steffen Oehlenschlaeger, Ludwigshafen (DE); Wolfgang Mackenroth, Bad Duerkheim (DE); Konrad Morgenschweis, Dresden (DE); Ulrich Penzel, Tettau (DE); Bernd Weidner, Wormlage (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 197 days.

(21) Appl. No.: 10/500,862

(22) PCT Filed: Jan. 30, 2003

(86) PCT No.: PCT/EP03/00924

§ 371 (c)(1),
(2), (4) Date: Jul. 20, 2004

(87) PCT Pub. No.: WO03/066571

PCT Pub. Date: Aug. 14, 2003

(65) Prior Publication Data

US 2005/0177003 A1    Aug. 11, 2005

(30) Foreign Application Priority Data

Feb. 6, 2002    (DE) ................. 102 04 700

(51) Int. Cl.
*C07C 209/36* (2006.01)
(52) U.S. Cl. ........................................ 564/422
(58) Field of Classification Search ................. 564/422
See application file for complete search history.

(56) References Cited

FOREIGN PATENT DOCUMENTS

| | | |
|---|---|---|
| CN | 1 377 875 | 11/2002 |
| DE | 28 35 943 | 3/1980 |
| DE | 32 45 318 | 6/1984 |
| EP | 052 719 | 6/1982 |
| EP | 634 391 | 1/1995 |
| WO | 00/35852 | 6/2000 |

*Primary Examiner*—Kamal A. Saeed
(74) *Attorney, Agent, or Firm*—Oblon, Spivak, McClelland, Maier & Neustadt, P.C.

(57) ABSTRACT

The invention provides a process for preparing amines by catalytic hydrogenation of nitroaromatics and subsequent removal of the catalysts from the reaction mixture, which contains at least one aromatic amine and water, which comprises carrying out the removal of the catalysts by means of membrane filtration, which is carried out at a pressure on the suspension side of from 5 to 50 bar, a pressure difference between the suspension side and the permeate side of at least 0.3 bar and a flux rate on the suspension side of from 1 to 6 m/s.

8 Claims, No Drawings

METHOD FOR THE PRODUCTION OF AMINES

The present invention relates to a continuous process for preparing amines, in particular aromatic amines, by catalytic hydrogenation of the nitro compounds on which the amines are based.

The preparation of amines, in particular of aromatic mono- and/or polyamines, by catalytic hydrogenation of the corresponding mono- and/or polynitro compounds has been known for some time and described many times in the literature.

The customary industrial preparation of the aromatic mono- and/or polyamines by reaction of nitro compounds with hydrogen liberates a considerable amount of heat. In industry, the hydrogenation is therefore usually carried out at very low temperatures in the liquid phase in the presence of hydrogenation catalysts. The compound to be reduced is mixed with the catalyst in a solvent and reduced batchwise in an autoclave or continuously in a loop reactor, a bubble column or a reactor battery. These known processes have a number of disadvantages, for example the necessity to remove the deactivated catalyst fractions, in particular in continuous processes, which results in catalyst losses. Furthermore, the side reactions which frequently occur result in the formation of interfering substances, for example tar-like constituents, which leads to reductions in yields, and are a problem in many processes used hitherto.

EP-A-634 391 describes a process for hydrogenating aromatic polynitro compounds to give amines, which is said to minimize the abovementioned problems of hydrogenation of aromatic polynitro compounds through technological optimization using a loop-Venturi reactor equipped with an ejector, coupled with specific conditions, such as a precise circulation volume ratio, precise energy input and a precisely adjusted hydrogen volume flow rate. The catalysts used are known hydrogenation catalysts, preferably metals from transition group VIII of the Periodic Table, in particular Raney iron, Raney cobalt and Raney nickel.

This process may, as a result of a heat exchanger for dissipating the heat of reaction being located outside the loop reactor, give rise to overheating in the ejector and in the reactor, which results in immediate onset of side reactions such as ring hydrogenations, hydrogenolytic dissociations or the formation of high molecular weight, tar-like products which coat the catalyst surface. In addition, a pure bubble-column character relating to the flow and residence time behavior, which involves random small- and large-volume vortexes with comparatively low mass transfer performance, becomes established in the reactor volume outside the ejector. There is therefore virtually no significant improvement in hydrogenation yields, hydrogenation selectivity and space-time yield in this process. In addition, circulation by pumping of the entire reaction mixture subjects the catalyst to high mechanical stresses, which again results in a reduced on-stream time of the catalyst.

WO 00/35852 describes a process for preparing amines by hydrogenation of nitro compounds. This process involves carrying out the reaction in a vertical reactor equipped with a downwardly pointing jet nozzle, through which the reactants and also the reaction mixture are fed, an external circuit, through which the reaction mixture is fed into the jet nozzle, and also a flow reversal means at the lower end of the reactor. The discharge of the end product is preferably effected via a removal unit for the catalyst. Suggested examples of useful removal units include settlers, filter units and centrifuges.

This process allows the selectivity and the space-time yields of hydrogenations to distinctly increase. However, for industrial scale hydrogenation, a further improvement of the process is desirable. A very high degree of removal of the hydrogenation catalyst used is in particular decisive for the economic viability of the process. Complete removal of the catalyst from the reaction mixture discharged from the reactor simplifies the workup of the end product. The removed catalyst may be fed back into the reactor and therefore does not need to be replaced by fresh catalyst. This is particularly important when noble metal catalysts are used.

It is known that catalysts may be removed by means of a crossflow filtration. This method of removal leads to a particularly gentle removal of the catalyst.

DE 32 45 318 discloses carrying out the removal of catalysts in gas/liquid reactions by means of a microfilter operated according to the crossflow principle. In order to minimize the stress on the catalyst, the filtration is operated at pressures of at least 10 bar on the suspension side and pressure differentials between the suspension side and the filtrate side of at maximum 6 bar and also temperatures in the range from 80 to 200° C.

DE 30 40 631 describes the removal of catalysts from reaction mixtures by means of membrane filtration and mentions that this process may also be used in the hydrogenation of nitroaromatics. The filters used are hollow fibers. The filtration is carried out at very low temperatures.

It is an object of the invention to develop a process for removing catalysts in the hydrogenation of nitroaromatics to give aromatic amines which allows a complete and gentle removal of the catalysts and allows the removed catalyst to be returned from the separating step into the reactor in its entirety.

We have found that, surprisingly, this object is achieved by carrying out the removal of the catalyst by means of a crossflow filter, which is embodied by a membrane filter, at a pressure on the suspension side of from 5 to 50 bar, preferably from 10 to 30 bar, a pressure difference between the suspension side and the permeate side of at least 0.3 bar and a flux rate on the suspension side of from 1 to 6 m/s.

The invention accordingly provides a process for preparing amines by catalytic hydrogenation of nitroaromatics and subsequent removal of the catalysts from the reaction mixture, which contains at least one aromatic amine and water, which comprises carrying out the removal of the catalysts by means of membrane filtration, at a pressure on the suspension side of from 5 to 50 bar, preferably from 10 to 30 bar, a pressure difference between the suspension side and the permeate side of at least 0.3 bar and a flux rate on the suspension side of from 1 to 6 m/s.

For the purposes of the present invention, the suspension side refers to the side of the membrane filter on which the catalyst-containing mixture is located, and the permeate side to the side of the membrane filter on which the catalyst-free mixture is located.

To carry out the process according to the invention and recover a catalyst-free product stream, the effluent from the hydrogenation reactor is brought into contact with a membrane and permeate (filtrate) is removed on the reverse side of the membrane at a lower pressure than on the side on which the catalyst-containing reaction mixture is located. This provides a catalyst concentrate (retentate) which may be returned to the synthesis reactor without further workup and a virtually catalyst-free permeate which comprises the reaction product, the aromatic amine in the process according to the invention, and also water and, if used, solvent.

The filtration according to the invention may be carried out continuously or batchwise.

The continuous operation of the process involves at least a partial stream of the reaction mixture being constantly passed through a membrane filter. When this embodiment of the process according to the invention is used, preference is given to locating the membrane filter in the external circuit of a circulation reactor. Preference is given to this embodiment of the process according to the invention.

The batchwise operation of the filtration according to the invention involves conducting the reaction mixture through a hookup purification stage comprising a membrane filter and its own circulation pump. Another embodiment of the batchwise filtration involves the reaction mixture being passed through a membrane filter after the reaction. This embodiment is less preferred, since the catalyst separated off in this case has to be concentrated more highly.

The filter membranes used in the process according to the invention, depending upon the particle size of the catalyst used, preferably have pore diameters in the range from 10 nm to 20 μm, in particular in the range from 50 nm to 10 μm and preferably from 100 nm to 5 μm.

The separating layers of the filter membranes may comprise organic polymers, ceramic, metal, carbon or combinations thereof and must be stable in the reaction medium and at the process temperature. For mechanical reasons, the separating layers are generally applied to a mono- or multilayer porous substructure, which may be of the same material as the separating layer or of at least one differing material. Preference is given to inorganic membranes on account of high synthesis temperature and the associated high temperature of the filtered reaction mixture. Examples include metal separating layers and metal substructures, ceramic separating layers and metal, ceramic or carbon substructures, polymer separating layers and polymer, metal, ceramic or ceramic on metal substructures. Examples of ceramics which are used include $\alpha$-$Al_2O_3$, $\gamma$-$Al_2O_3$, $ZrO_2$, $TiO_2$, SiC or mixed ceramic materials. Examples of polymers which may be used include polytetrafluoroethylene, polyvinylidene fluoride (PVDF), polysulfone, polyethersulfone, polyetheretherketone and polyamide.

The membranes are customarily mounted in pressure-rated casings which allow separation of the retentate (catalyst-containing) from the permeate (catalyst-free filtrate) under the pressure conditions necessary for the filtration. The membranes may have flat, tubular, multichannel element, capillary or wound geometries, for which appropriate pressure casings which allow separation of the retentate from the permeate are available. Depending on the area requirements, a filter element may comprise plural channels. More than one of these elements may also be combined within a casing to give a module.

In a preferred embodiment, metal membranes are used which are welded to the casings.

Preference is given to operating the process so that as far as possible no cake layers form on the suspension side of the membrane. If disrupting cake layers form, through which the filtration is compromised, it is possible to remove these by flow reversal between suspension side and permeate side. The flow reversal can be achieved in particular by increasing the permeate pressure to above the retentate pressure.

Optimal transmembrane pressures between the retentate and permeate, depending on the diameter of the membrane pores, the hydrodynamic conditions which influence the buildup of cake layers, the mechanical stability of the membrane and the operating temperature, and the type of membrane, are substantially at least 0.3 bar, in particular from 0.5 to 50 bar, preferably from 1 to 25 bar.

Relatively high transmembrane pressures usually lead to relatively high permeate fluxes. Since the synthesis effluent is usually introduced directly to the membrane filtration step at the synthesis presssure, the transmembrane pressure may be reduced, by increasing the permeate pressure, to a value smaller than the synthesis pressure.

Since the synthesis temperature is predetermined by the process and is above 80° C., the membrane has to be stable at this temperature. Relatively high temperatures lead in principle to relatively high permeate fluxes and are therefore preferred.

When, in specialized applications of the process according to the invention, membranes have to be used which are unstable at these temperatures, the reaction mixture has to be cooled before the filtration and the retentate before introduction into the reactor has to be heated again. This embodiment is not preferred.

The achievable permeate fluxes depend strongly upon the membrane type and geometry used, the process conditions, the suspension composition, the catalyst concentration and catalyst type. The fluxes are customarily from 20 to 500 $kg/m^2/h$.

The process according to the invention allows a catalyst retention of >99% to be achieved.

The process according to the invention allows all catalysts which may be used for the hydrogenation of nitroaromatics to be removed. Useful catalysts include metals of transition group VIII of the Periodic Table, which may be applied to support materials such as carbon or oxides of aluminum, silicon or other materials. Preference is given to using Raney nickel and/or supported catalysts based on nickel, palladium, iridium and/or platinum on carbon supports. The process can particularly advantageously be used for removing catalysts in which little of the highly fused by-products, frequently referred to as "tar", occur. This tar may cause blockages of the membrane used and reduce the lifetime of the filter. Since noble metal catalysts operate particularly selectively and the hydrogenation of nitroaromatics only forms very little high molecular weight tar, the removal of the noble metal catalysts by means of membrane filtration is particularly advantageous.

The average particle size of the catalysts used is usually in the range from 10 nm to 200 μm, in particular in the range from 50 nm to 100 μm and preferably from 100 nm to 30 μm.

The hydrogenation of the aromatic nitro compounds may be effected by the customary and known processes.

This involves, independent of the type of the nitro compounds used, a pressure of from 5 to 50 bar, preferably from 10 to 30 bar, and an operating temperature of from 80 to 200° C., preferably from 100 to 180° C., being maintained with preference in the reactor.

The mono- and/or polynitro compound may be used in pure form, as a mixture with the corresponding mono- and/or polyamine, as a mixture with the corresponding mono- and/or polyamine and water or as a mixture with the corresponding mono- and/or polyamine, water and a solvent, in particular an alcohol. The aromatic mono- and/or polynitro compound is introduced to the mixture in highly divided form. The reaction mixture which leaves the reactor comprises water which is by-produced during the hydrogenation.

The reactors used include the customary and known hydrogenation reactors. Examples include stirred tanks, bubble columns, which may contain packings, or loop reactors, such as loop-Venturi reactors or jet loop reactors having internal and external circuits, as described, for example, in WO 00/35852.

The process according to the invention may particularly advantageously be applied to the removal of catalysts when loop reactors having an external circuit are used. In this case, the membrane filter is located in the external circuit.

A particularly preferred embodiment of the process according to the invention involves the use of a hydrogenation reactor as described in WO 00/35852. This embodiment does not require an additional pump for the membrane filtration, since the necessary pressure on the suspension side may be maintained by the pump for the external circuit. This allows the process to be distinctly simplified. Also, the use of such reactors makes complete conversion of the nitroaromatics possible so that the subsequent workup after the complete removal of the catalyst becomes particularly simple. This process utilizes particularly well the advantages of noble metal catalysts, in particular those based on platinum, palladium and/or iridium, namely high activity and good selectivity.

For the purposes of the present invention, preference is given to using aromatic nitro compounds having one or more nitro groups and from 6 to 18 carbon atoms, for example nitrobenzenes, such as o-, m- or p-nitrobenzene, 1,3-dinitrobenzene, nitrotoluenes, e.g. 2,4- or 2,6-dinitrotoluene, 2,4,6-trinitrotoluene, nitroxylenes, e.g. 1,2-dimethyl-3-, 1,2-dimethyl-4-, 1,4-dimethyl-2-, 1,3-dimethyl-2-, 2,4-dimethyl-1- and 1,3-dimethyl-5-nitrobenzene, nitronaphthalenes, e.g. 1- or 2-nitronaphthalene, 1,5 and 1,8-dinitronaphthalene, chloronitrobenzenes, e.g. 2-chloro-1,3- or 1-chloro-2,4-dinitrobenzene, o-, m- or p-chloronitrobenzene, 1,2-dichloro-4-, 1,4-dichloro-2-, 2,4-dichloro-1- and 1,2-dichloro-3-nitrobenzene, chloronitrotoluenes, e.g. 4-chloro-2-, 4-chloro-3-, 2-chloro-4- and 2-chloro-6-nitrotoluene, nitroanilines, e.g. o-, m- or p-nitroaniline; nitroalcohols, e.g. tris(hydroxymethyl)nitromethane, 2-nitro-2-methyl- or 2-nitro-2-ethyl-1,3-propanediol, 2-nitro-1-butanol or 2-nitro-2-methyl-1-propanol, and also any mixtures of two or more of the nitro compounds mentioned.

Preference is given to hydrogenating aromatic nitro compounds, preferably mononitrobenzene, methylnitrobenzene or methylnitrotoluene, and in particular 2,4-dinitrotoluene or its industrial mixtures with 2,6-dinitrotoluene, with these mixtures preferably having up to 35 percent by weight, based on the overall mixture, of 2,6-dinitrotoluene with fractions of from 1 to 4 percent of vicinal DNT and from 0.5 to 1.5% of 2,5- and 3,5-dinitrotoluene, to give the corresponding amines.

The invention is illustrated by the following examples.

EXAMPLE 1 AND COMPARATIVE EXAMPLE 2

Hydrogenation of Dinitrotoluene

In a 5 l jet loop reactor equipped with a circulation pump, jet nozzle, internal tube and heat exchanger, the dinitrotoluene was hydrogenated over a supported nickel catalyst having an average particle size of from 5 to 10 µm at 120° C. and 25 bar. The activity of the catalyst was constantly monitored by gas chromatography analysis samples and when necessary, further catalyst was metered in. The concentration of catalyst was 3% by weight, based on the reaction mixture.

The removal of the catalyst from the reaction mixture was effected either by a membrane filter (inventive) or by a settler (comparative).

EXAMPLE 1

Membrane Filtration

A cylinder made of highly porous ceramic having a length of 750 mm and a lengthwise channel having a diameter of 6 mm, on whose surface the actual filtering membrane made of zirconium dioxide having a pore size of 50 nm was applied. The suspension to be treated flowed with a flux rate of 4 m/s in the channel along the membrane, and a partial stream passed through the membrane as permeate and was removed through the ceramic support material. The transmembrane pressure was 2 bar, the permeate flux 440 l/m$^2$/h.

COMPARATIVE EXAMPLE 2

Gravitational Separator (Settler)

A partial stream of the circulation stream (reactor-circulation pump-nozzle) was diverted using the initial pressure of the circulation pump to the lower part of a settler and passed from there back into the reactor according to the mass flows without an additional conveying element.

The actual reactor effluent (settler effluent) flowed upwardly through a separating tube at an angle of 55° and, controlled by the liquid level and gas content in the reactor, was discharged through a pressure relief valve. The flux ratios in the separator lamella were set so that all particles larger than 1 µm were separated and fell down to the bottom of the settler, from where they were transported by the circulation flow (settler recycling) back into the reactor. Smaller particles were passed out with the end product.

Results

In two series of experiments, the reactor was operated once equipped with a gravity separator (comparative experiment) and once equipped with membrane filtration (inventive).

Using a gravity separator, a space-time yield of 250–350 kg of TDA/(m$^3$·h) was achieved over a period of 4 weeks. 400 to 600 g of catalyst were consumed per metric ton of TDA.

Using membrane filtration, a space-time yield of 400 to 500 kg of TDA/(m$^3$·h) was achieved over a period of 3 months. 350 to 450 g of catalyst were consumed per metric ton of TDA.

EXAMPLES 3 AND 4

The devices described in Example 1 for hydrogenation and catalyst removal were used and the effectiveness of different catalysts at different reaction temperatures in the hydrogenation of nitrobenzene was tested.

EXAMPLE 3

The catalyst from Example 1 was used in a concentration of 2% by weight, based on the reaction mixture. The transmembrane pressure was 1 bar, the permeate flux 200 l/m$^2$/h.

At 140° C., a space-time yield of 800 kg/(M$^3$·h) was achieved at a selectivity of 99.7%, and at 180° C., a space-time yield of 1800 kg/(m$^3$·h) was achieved at a selectivity of 98.3%.

EXAMPLE 4

A catalyst comprising 5% by weight of platinum and 2% by weight of iron on activated carbon having an average particle size of from 20 to 30 μm in a concentration of 2% by weight, based on the reaction mixture, was used. The transmembrane pressure was 1 bar, the permeate flux 200 $l/M^2/h$.

At 140° C., a space-time yield of 1500 kg/(m³·h) at a selectivity of 99.82% was achieved. At 180° C., a space-time yield of 2200 kg/(m³·h) at a selectivity of 99.6% was achieved.

We claim:

1. A process for preparing amines by catalytic hydrogenation of nitroaromatics and subsequent removal of the catalysts from the reaction mixture, which contains at least one aromatic amine and water, which comprises carrying out the removal of the catalysts continuously by means of membrane filtration, which is carried out at a pressure on the suspension side of from 5 to 50 bar, a pressure difference between the suspension side and the permeate side of at least 0.3 bar and a flux rate on the suspension side of from 1 to 6 m/s.

2. A process as claimed in claim 1, wherein the pressure on the suspension side is from 10 to 30 bar.

3. A process as claimed in claim 1, wherein the filter membrane has a pore diameter in the range from 10 nm to 20 μm.

4. A process as claimed in claim 1, wherein the hydrogenation is carried out in a jet loop reactor.

5. A process as claimed in claim 1, wherein the hydrogenation is carried out in a jet loop reactor having an external and an internal circuit.

6. A process as claimed in claim 1, wherein the catalysts used comprise metals of transition group VIII of the Periodic Table on supports.

7. A process as claimed in claim 1, wherein the catalysts used comprise platinum, palladium and/or iridium catalysts on carbon supports.

8. A process as claimed in claim 1, wherein the hydrogenation is carried out in a jet loop reactor having an external and internal circuit, the catalysts used comprise platinum, palladium and/or iridium catalysts on carbon supports and the membrane filter is located in the external circuit of the reactor.

* * * * *